(12) United States Patent
Dally

(10) Patent No.: US 11,964,541 B1
(45) Date of Patent: Apr. 23, 2024

(54) MULTI-PASSENGER VEHICLE VENTILATION SYSTEM

(71) Applicant: James Edwin Dally, Kalamazoo, MI (US)

(72) Inventor: James Edwin Dally, Kalamazoo, MI (US)

(73) Assignee: James Edwin Dally, Kalamazoo, MI (US)

(*) Notice: Subject to any disclaimer, the term of this patent is extended or adjusted under 35 U.S.C. 154(b) by 0 days.

(21) Appl. No.: 18/196,254

(22) Filed: May 11, 2023

(51) Int. Cl.
*B60H 1/24* (2006.01)
*A61L 9/20* (2006.01)
(Continued)

(52) U.S. Cl.
CPC ............. *B60H 1/245* (2013.01); *A61L 9/20* (2013.01); *B60H 1/00321* (2013.01);
(Continued)

(58) Field of Classification Search
CPC ......... F24F 8/22; B60H 1/245; B60H 3/0071; B60H 1/247; B60H 1/3407; B60H 1/00371; B60H 2001/0022; A61L 9/20; A61L 2209/12; A61L 2209/212; B60N 2/5657; B60N 2/565
(Continued)

(56) References Cited

U.S. PATENT DOCUMENTS

| 3,862,549 A | * | 1/1975 | Fernandes | .......... B61D 27/0018 |
|---|---|---|---|---|
| | | | | 165/42 |
| 4,807,523 A | * | 2/1989 | Radtke | ...................... B60S 1/54 |
| | | | | 296/97.5 |

(Continued)

FOREIGN PATENT DOCUMENTS

| CN | 111301113 A | * | 6/2020 |
|---|---|---|---|
| CN | 114161903 A | * | 3/2022 |

(Continued)

OTHER PUBLICATIONS

CN 111688436 Zou et al automobile air conditioner and automobile with the same published Sep. 22, 2020 (Year: 2020).*

(Continued)

*Primary Examiner* — Edelmira Bosques
*Assistant Examiner* — Frances F. Hamilton
(74) *Attorney, Agent, or Firm* — Vorys, Sater, Seymour and Pease, LLP

(57) ABSTRACT

A ventilation system for a vehicle having a cabin includes a segmented plenum comprising a plurality of sub-plenums that are disposed above the cabin, a perforated panel defining the ceiling of the cabin and having plurality of perforations for air communication of the plenum with the cabin, and ductwork including one or more upper main ducts, lower main ducts, vertical ducts, and seat return ducts. The ducts communicate with each other to convey air, descending from the segmented plenum through the perforated panel as a high volume, low turbulence blanket of air through the cabin, back to the segmented plenum. The ventilation system also includes an air processing unit (APU) in communication with the ductwork and operable to sterilize the air conveyed therein, and one or more fans for circulating the air in the ventilation system.

22 Claims, 6 Drawing Sheets

(51) Int. Cl.
   *B60H 1/00* (2006.01)
   *B60H 3/00* (2006.01)
   *B60N 2/56* (2006.01)
   *F24F 8/22* (2021.01)
   *B60H 3/06* (2006.01)
(52) U.S. Cl.
   CPC ......... B60H 3/0071 (2013.01); B60N 2/5657 (2013.01); F24F 8/22 (2021.01); *A61L 2209/12* (2013.01); *A61L 2209/212* (2013.01); *B60H 2003/0675* (2013.01); *B60N 2/565* (2013.01)
(58) Field of Classification Search
   USPC .......................................................... 454/137
   See application file for complete search history.

(56) References Cited

U.S. PATENT DOCUMENTS

| | | | | |
|---|---|---|---|---|
| 5,054,378 | A * | 10/1991 | Speece | B60H 1/00371 62/244 |
| 5,389,035 | A * | 2/1995 | Ishida | B61D 27/0018 454/115 |
| 5,450,894 | A * | 9/1995 | Inoue | B60H 1/00842 454/907 |
| 6,497,275 | B1 * | 12/2002 | Elliot | B60H 1/246 165/204 |
| 6,709,328 | B1 * | 3/2004 | Jain | B60H 1/00371 454/83 |
| 7,029,065 | B2 * | 4/2006 | Laib | B60H 1/248 297/180.13 |
| 2001/0029162 | A1 * | 10/2001 | Yoshinori | B60H 1/247 454/140 |
| 2006/0116064 | A1 * | 6/2006 | Umebayashi | B60H 1/3407 454/143 |
| 2011/0297659 | A1 * | 12/2011 | Bixler | B60H 1/2225 219/201 |
| 2016/0229277 | A1 * | 8/2016 | Le Bastard | B60J 9/04 |
| 2018/0079278 | A1 * | 3/2018 | Kirpichnikov | B60H 1/00742 |
| 2019/0077215 | A1 * | 3/2019 | Baek | B60H 1/246 |
| 2019/0329797 | A1 * | 10/2019 | Davis | B60H 1/00371 |
| 2020/0023708 | A1 * | 1/2020 | Mullen | B60H 1/00564 |
| 2021/0016216 | A1 * | 1/2021 | Popa-Simil | F24F 3/167 |
| 2021/0070133 | A1 * | 3/2021 | Laux | B60H 1/00821 |

FOREIGN PATENT DOCUMENTS

| | | | | | |
|---|---|---|---|---|---|
| DE | 19832738 | A1 * | 1/2000 | | B60H 1/00564 |
| DE | 102013018555 | A1 * | 5/2015 | | B60H 1/00792 |
| DE | 102016202291 | A1 * | 8/2017 | | |
| EP | 1769953 | A2 * | 4/2007 | | B60H 1/00371 |
| EP | 3945004 | A1 * | 2/2022 | | |
| GB | 2234801 | B1 * | 3/1989 | | |
| GB | 3945004 | A1 * | 7/2020 | | |
| KR | 1020130031164 | A * | 3/2013 | | |

OTHER PUBLICATIONS

JP H0569824 Ishida Takeshi et al ventilating device for vehicle Mar. 23, 1993 (Year: 1993).*

DE 102016202291 Bouchanmi et al air conditioning, vehicle with the air conditioning and method of controlling the air conditionoing Aug. 17, 2017 (Year: 2017).*

DE 3302423 Weidinger et al Einrightung zum klimatisieren con reisezugwagen Jul. 26, 1984 (Year: 1984).*

EP 1769953 Guelke et al hot and cold air apparatus for buses Apr. 4, 2007 (Year: 2007).*

DE 19832738 Rassaerts Saloon of vehicle for transportation of people . . . Jan. 27, 2000 (Year: 2000).*

* cited by examiner

MULTI-PASSENGER VEHICLE VENTILATION SYSTEM

TECHNICAL FIELD

The present disclosure relates generally to ventilation systems, and more particularly, to multi-passenger vehicle ventilation systems.

BACKGROUND

In the wake of the Covid-19 pandemic, governments spent billions of dollars and there are still unspent billions to address making public places and services, such as transportation, safer. While schools may have been made safer with increased air exchange, children are still spending extended periods of time on school buses sneezing, coughing, and discharging respiratory droplets (e.g., spitting) on each other while traveling to and from school. To fully protect our children and their safety this school bus exposure needs to be addressed.

Similarly, in public transportation, public buses ferrying passengers daily to and from jobs and on innumerable short and long term trips expose the passengers to unnecessary risk by intermixing the air they breathe and distributing any germs and biological material among, contributing to spread of respiratory and other diseases, including Covid-19. Occupants of other confined spaces, and particularly vehicles such airplanes, boats, vans, and the like are similarly at risk and need to be protected.

Conventionally, airplane ventilation or other vehicle (e.g., automobile, bus, etc.) and building heating and ventilation systems use high velocity to blow the air into the space and intentionally stir up the air to balance and evenly distribute air temperature. Even a downdraft technology paint booth or lab hood draws and moves air at a high velocity and turbulence. All of these high velocity air forcing distribution methods compromise the air quality of the cabin or room and arguably spread and distribute pathogens, causing more harm than good to occupants.

There is a long-felt need for a cabin or interior space ventilation system, for example for a multi-passenger vehicle such as a bus, that does not agitate the interior air and distribute pathogens, but that still circulates and replaces the air with conditioned air that may be heated, cooled, purified, and/or sterilized as the need may be. "Conditioned air," as used herein, may be defined as air that has been treated in any of one or more ways such as circulating, heating, cooling, humidifying, dehumidifying, sterilizing, ionizing, filtering, augmenting or replacing with exterior air, or the like.

OVERVIEW

Described herein is a ventilation system for a vehicle having a cabin for transporting passengers. The ventilation system includes a segmented plenum comprising a plurality of sub-plenums that are disposed above the cabin, a perforated panel defining the ceiling of the cabin and having plurality of perforations for air communication of the plenum with the cabin, and ductwork including one or more upper main ducts, one or more lower main ducts, one or more vertical ducts, and one or more seat return ducts. The upper main ducts, lower main ducts, vertical ducts and seat return ducts communicate with each other to convey air, descending from the segmented plenum through the perforated panel as a high volume, low turbulence blanket of air through the cabin, back to the segmented plenum. The ventilation system also includes an air processing unit (APU) in communication with the ductwork and operable to sterilize the air conveyed therein, and one or more fans for circulating the air in the ventilation system.

Also described herein is a vehicle having the ventilation system set forth above.

Also described herein is a method for ventilating a cabin of a vehicle. The method includes balancing air pressure in a plurality of sub-plenums disposed above a cabin and separated therefrom by a perforated panel such that a high volume, low turbulence blanket of air descends through the cabin, capturing and conditioning the descended air before re-introducing it into the sub-plenums.

BRIEF DESCRIPTION OF THE DRAWINGS

The accompanying drawings, which are incorporated into and constitute a part of this specification, illustrate one or more examples of embodiments and, together with the description of example embodiments, serve to explain the principles and implementations of the embodiments.

In the drawings.

DESCRIPTION OF EXAMPLE EMBODIMENTS

Figure 1:
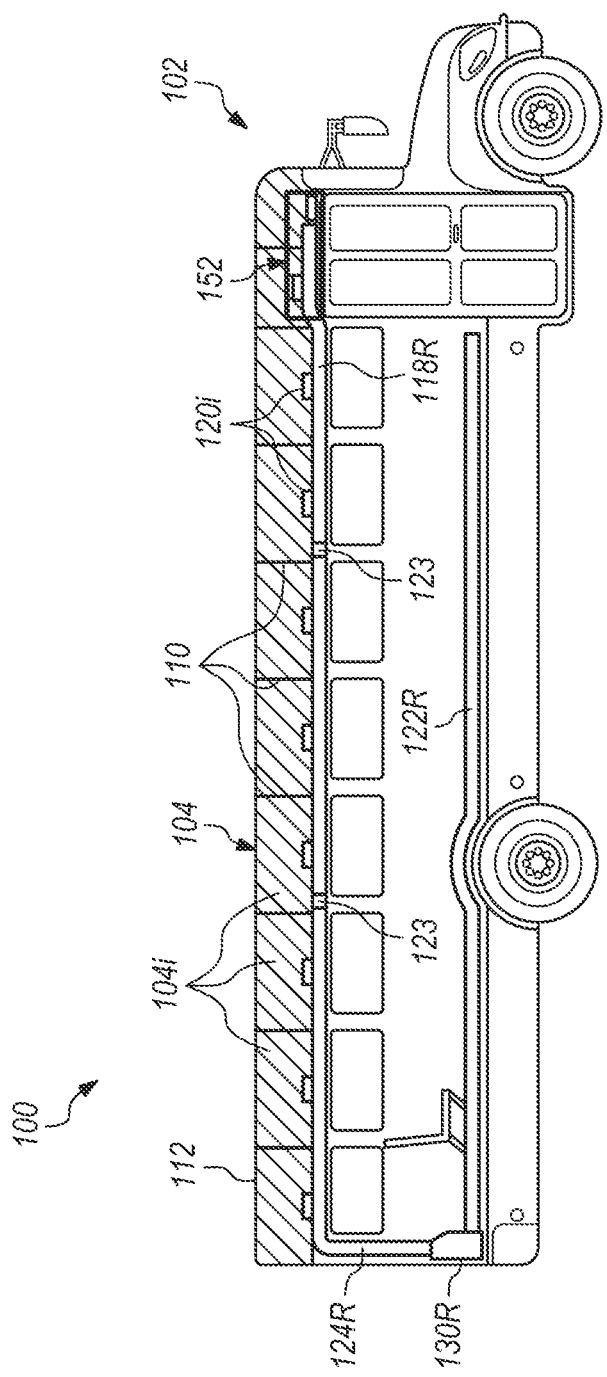
FIG. 1 is a schematic diagram of a multi-passenger vehicle ventilation system for use in a vehicle such as a school bus in accordance with certain embodiments.

Example embodiments are described herein in the context of vehicle ventilation systems, and more particularly, multi-passenger vehicle ventilation systems. The following description is illustrative only and is not intended to be in any way limiting. Other embodiments will readily suggest themselves to those of ordinary skill in the art having the benefit of this disclosure. Reference will be made in detail to implementations of the example embodiments as illustrated in the accompanying drawings. The same reference indicators will be used to the extent possible throughout the drawings and the following description to refer to the same or like items.

In the description of example embodiments that follows, references to "one embodiment", "an embodiment", "an example embodiment", "certain embodiments," etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to effect such feature, structure, or characteristic in connection with other embodiments whether or not explicitly described. The term "exemplary" when used herein means "serving as an example, instance or illustration." Any embodiment described herein as "exemplary" is not necessarily to be construed as preferred or advantageous over other embodiments.

In the interest of clarity, not all of the routine features of the implementations described herein are shown and described. It will be appreciated that in the development of any such actual implementation, numerous implementation-specific decisions must be made in order to achieve the developer's specific goals, such as compliance with application- and business-related constraints, and that these specific goals will vary from one implementation to another and from one developer to another. Moreover, it will be appreciated that such a development effort might be complex and time-consuming, but would nevertheless be a routine undertaking of engineering for those of ordinary skill in the art having the benefit of this disclosure.

Herein, "or" is inclusive and not exclusive, unless expressly indicated otherwise or indicated otherwise by context. Therefore, herein, "A or B" means "A, B, or both," unless expressly indicated otherwise or indicated otherwise by context. Moreover, "and" is both joint and several, unless expressly indicated otherwise or indicated otherwise by context. Therefore, herein, "A and B" means "A and B, jointly or severally," unless expressly indicated otherwise or indicated otherwise by context.

Described herein is a "High Volume Low Turbulence" (HVLT) system for delivering air through a large plenum (one or more plenums or sub-plenums are contemplated) across substantially the entire top of a vehicle cabin's ceiling through an array of perforations. This approach allows the air, which is evenly pressurized within the plenum(s), to fall planarly, like a sheet across the entire cabin consistently, in blanket fashion.

In certain embodiments, "Air Processing Units" (APUs) are used to supply air. The air may be conditioned as appropriate for passenger comfort and safety, and such conditioning may include any one or more of heating, cooling, humidifying, dehumidifying, sterilizing, ionizing, filtering, augmenting or replacing with exterior air, or the like. The term "conditioning" will thus be used herein to denote any one or more of these actions.

In certain embodiments, two APU's are deployed in the multi-passenger vehicle. Reasons for this include 1) It allows the air plenum(s) to be equally pressurized from both sides, 2) it provides redundancy should one of the system's equipment fail, 3) It provides the most efficient and accurate air cycling of the cabin, and 4) It allows electric heating and air conditioning and other conditioning to be added via a module.

The APU entails a cabinet with a tamper proof access door which is equipped with a battle switch or circuit interrupter switch for safety of maintenance crew due to the dangers of exposure to UVC lighting which may be used for sterilization. The APU operates like a black out box so that there is no possibility of occupants being exposed to the UVC lighting. The APU is sized for the maximum amount of air exposure to the sterilizing UVC bulbs when used, and the bulbs may be designed to special wavelengths of nanometers depending on the targeted pathogens, such as Covid-19. The APU may be designed to expose the air in ratio to the proper UVC lighting in order to implement an effective sterilization regime. The APU can be equipped with both heating and cooling, or any conditioning equipment as that term is defined above.

In certain embodiments, there is a supply duct that comes off each APU and runs up a sidewall of the vehicle cabin and then runs down the side of the of the vehicle, on top of the windows to feed the plenum(s). In certain embodiments, this duct will be plastic so that it is extremely durable and blends with the interior decor of most multi-passenger vehicle cabins. Small in-line booster fans may be deployed within this ductwork to ensure that sub-plenums, when present, remain equally pressurized in a balanced manner.

In certain embodiments, a fully perforated ceiling panel may be implemented, to provide a high volume and low turbulent sheet of air that blankets down across the passengers in a substantially vertical route, carrying particulates down with it and substantially preventing them from dispersing laterally and spreading among passengers. This ceiling panel may have thousands of substantially equally spaced holes (apertures) that allow an even, yet slowly, controlled discharge of air. The plenum depth above the panel ranges from about one to three inches depending on the cabin height for instance.

In certain embodiments, a liquid ceramic heat reflective coating may be applied, as well as a liquid sound reducing coating on the inside bottom of the cabin roof skin.

The pressurized air plenum may be segmented into several "zoned" smaller sub-plenums with the use of small air dampers that allow controllable, even, balanced pressurization. Each sub-plenum may be balanced with manual dampers from the supply duct(s). This blanket of air then falls and is pulled into return air ducts that are located at the perimeter of each seat causing the wind to act like a shear. The air is then returned via a plastic ducting system that is mounted along the floor at both sides of the cabin with branch extensions that feed return ducts under the seats. The seats are equipped with return air ducts at the front, rear, and aisle end. All of this permits the air to be pulled down vertically directly in all areas especially in front of the occupants, which, vastly reduces lateral air motion and eliminates pathogen transfer throughout the air system of the cabin.

In certain embodiments, and for example depending on the geographic location of the vehicle, heat and/or air conditioning may be provided. In certain designs, for example in retrofit configurations of existing passenger vehicles, existing box heaters may be removed as they may cause undesired mixing of air that disrupts the blanket of air approach. In certain embodiments the existing heating element can be installed in an additional module attached to the APU as further detailed below.

In certain embodiments, an air screen or air door is located over the vehicle (e.g. school bus) main access door. This screen/air door can automatically come on (activate) upon the access door being opened. Advantages of such an arrangement are: 1) It prevents the loss of cooled or heated (or otherwise conditioned) air, thus increasing efficiency, 2) It prevents outside contamination from entering the cabin, and 3) It prevents insects from entering the cabin.

It will appreciated that while discussed primarily in terms of a school bus, the system is applicable to any type of multi-passenger vehicle cabin including, but not limited to, public transportation buses, aeronautical aircraft, tour buses, 15-passenger vans or the like, trains, subways, and so on.

Figure 2:
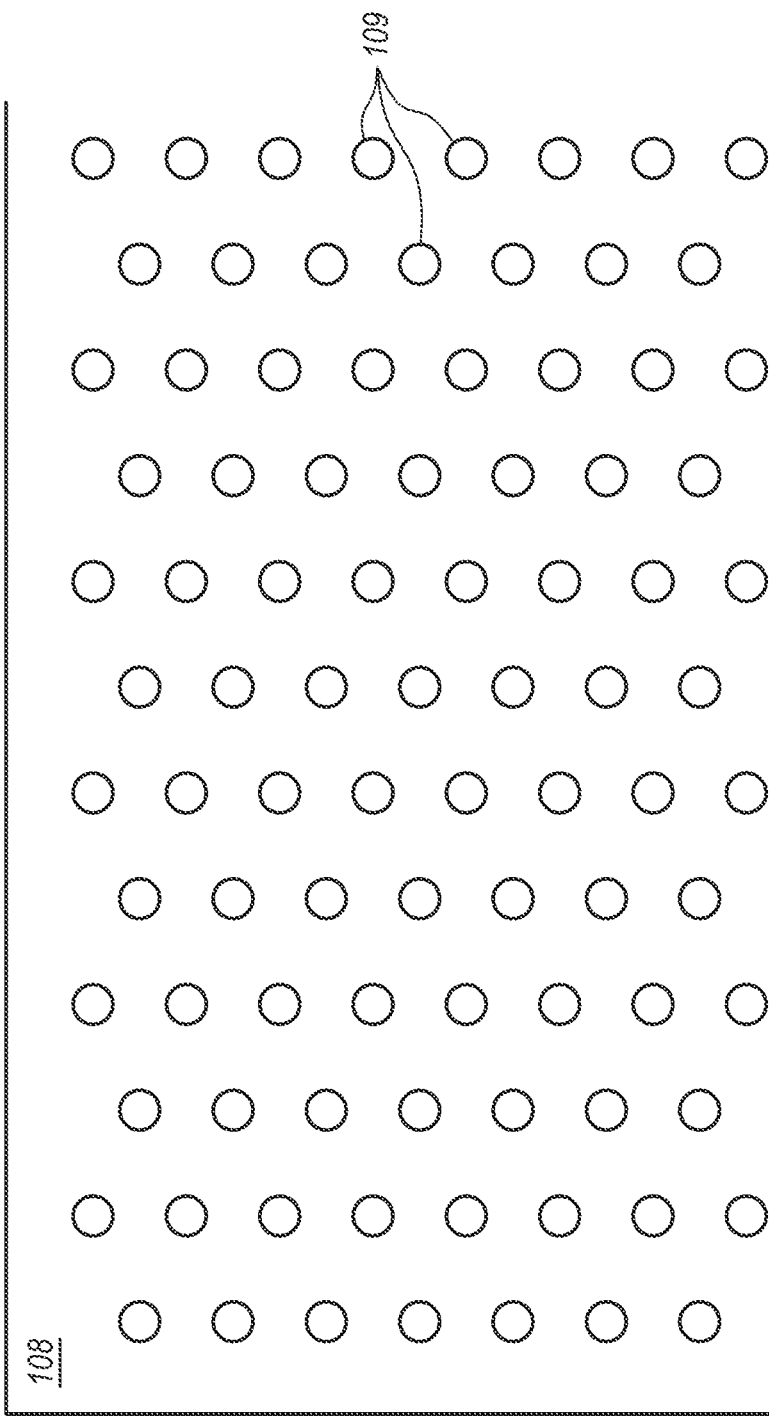
FIG. 2 is a schematic diagram of a perforated panel in accordance with certain embodiments.

FIG. 1 schematically depicts a multi-passenger vehicle ventilation system 100 for use in a vehicle, such as a school bus 102, in accordance with certain embodiments. Generally, the system 100 comprises a segmented plenum 104 from which pressurized conditioned air 106 (see FIG. 3) is delivered downward into the main passenger cabin through a perforated overhead panel 108 (see FIGS. 2 and 3). As seen in FIG. 2, perforations 109 defined in the overhead panel 108 may be formed in a regular, equidistantly-spaced pattern, although irregular patterns are also contemplated.

Figure 3:
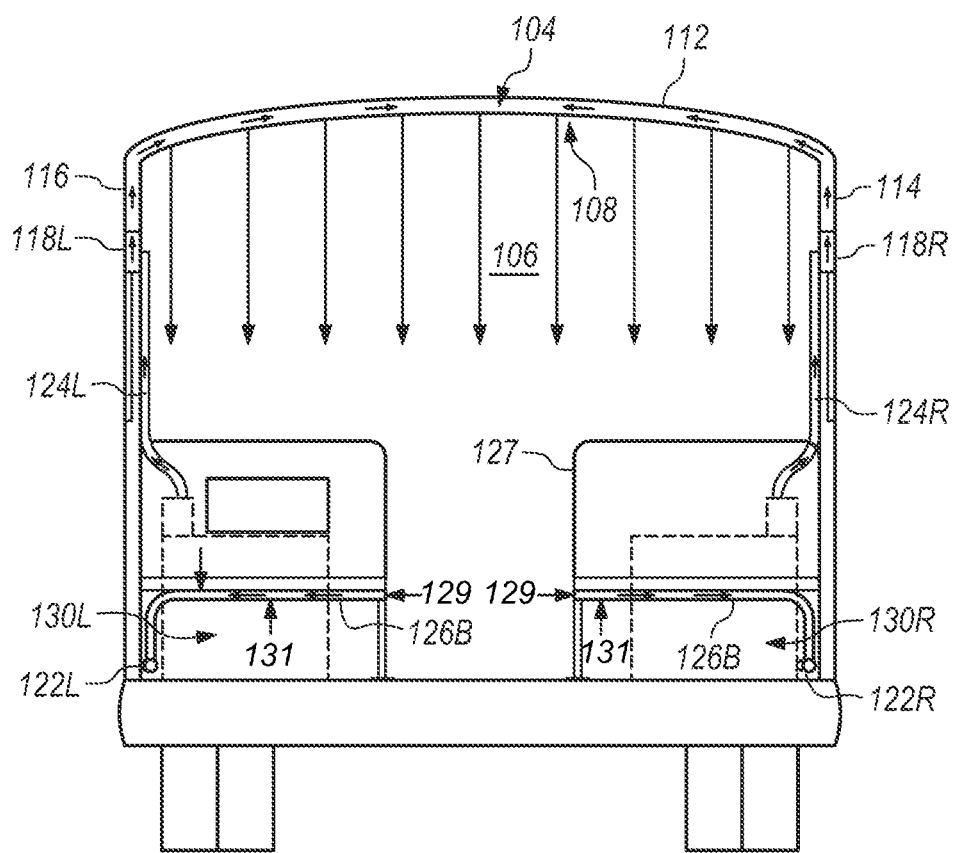
FIG. 3 is a cut-away rear view of a bus with a ventilation system in accordance with certain embodiments.

Returning to FIG. 1, a sequence of partitions 110, spaced apart 2-3 feet for example, effect the segmentation of the plenum 104 into, for example, ten sub-plenums 104$i$ that are substantially sealed from one another and disposed axially in sequence along the length of the bus 102. As best seen in FIG. 3, in certain embodiments, the panel 108 may be spaced about 1-3 inches from roof 112, generally following the contour of the roof at that spacing along its entire width from the right side 114 to the left side 116 of the bus 102, with the defined plenum 104 thereby having a corresponding consistent width of about 1-3 inches. In certain embodiments, one or more coatings (not shown) may be applied to the bottom surface of the roof 112, and within the plenum, for example in liquid form for heat and/or sound insulation for instance.

Air supply into the plenum 104 is provided by way of ductwork comprising a pair of upper main ducts 118R (right) and 118L (left) (collectively 118) that deliver air into each sub-plenum 104$i$ through dedicated balance valves 120$i$. Each sub-plenum 104$i$ may thus be supplied with air by a pair of balance valves 120$i$ (FIG. 1), one communicating with the upper main duct 118R and one communicating with the upper main duct 118L. At initial system setup, airflow through each valve 120$i$ is adjusted, for example through a valve adjustment mechanism such as a slide door, damper, or the like (not shown), to balance air pressure in the sub-plenums 104$i$ so that they are able to evenly deliver, through the perforated overhead panel 108, a high volume, low turbulence blanket of air (vertically) downwards into the cabin. Importantly, the inflow of air into the cabin through system 100 is substantially entirely by way of the plenum 104 and perforated panel 108, without contributions from the side of the vehicle. This results in an even, unagitated down flow of the air in the cabin, avoiding vortices and mixing of the air and its contents. Upper main ducts 118R and 118L may be made of plastic or other suitable material. Inline booster fans 123 (FIG. 1) may be provided in the ductwork, for example in upper main ducts 118R and 118L, to aid in movement of air through the ducts and provide air circulation. In certain embodiments the fans 123 may use brushless fan motors (not shown).

The ductwork of system 100 also comprises a pair of lower main ducts 122R (right) and 122L (left) (collectively 122) respectively in communication with upper main ducts 118R and 118L by way of vertical ducts 124R and 124L (collectively 124). Vertical ducts 124 may be made of plastic and generally run vertically up the back of the vehicle, in the back right and left corners thereof, to connect the respective upper main ducts 118 and lower main ducts 122. In certain embodiments, air circulation in the ductwork is facilitated by the inline booster fans 123 (FIG. 1), which aid in moving the air through the circuit, and sufficiently pressurize the plenum 104 to motivate the forced downward motion of air through the panel 108 as described above. The inline booster fans 123 may be powered by brushless motors (not shown) in some examples.

Figure 4:
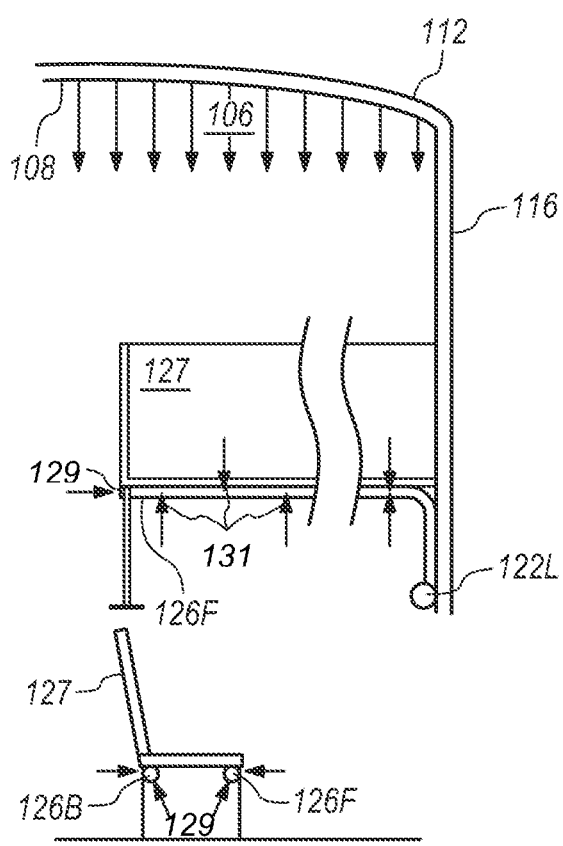
FIG. 4 is a partial cut-away front view of a bus with a ventilation system in accordance with certain embodiments.

Lower main ducts 122 may also be made of plastic or other suitable material and generally extend along the floor of the vehicle cabin, receiving air from a series of seat return ducts 126. In certain embodiments, and as best illustrated in FIGS. 3 and 4, two seat return ducts 126 are associated with each seat 127 of the vehicle—a front seat return duct 126F extending along the width of and beneath the seat at the front thereof, and a back seat return duct 126B extending along the width of and beneath the seat at the back thereof. The seat return ducts 126 have inlets 129 at the aisle ends thereof (the aisle is defined as the central space between the two rows of seats on either side of the vehicle), as well as at other intermediate locations 131 along their length and directed at different angles along their perimeter (or circumference in the case of tubular cross-sections). The inlets 129 are configured to receive cabin air descending vertically from the plenum 104, permitting the air to be pulled down vertically directly in substantially all areas especially in front of the occupants, which vastly reduces lateral air motion and eliminates pathogen transfer throughout the air system of the cabin.

Figure 5:
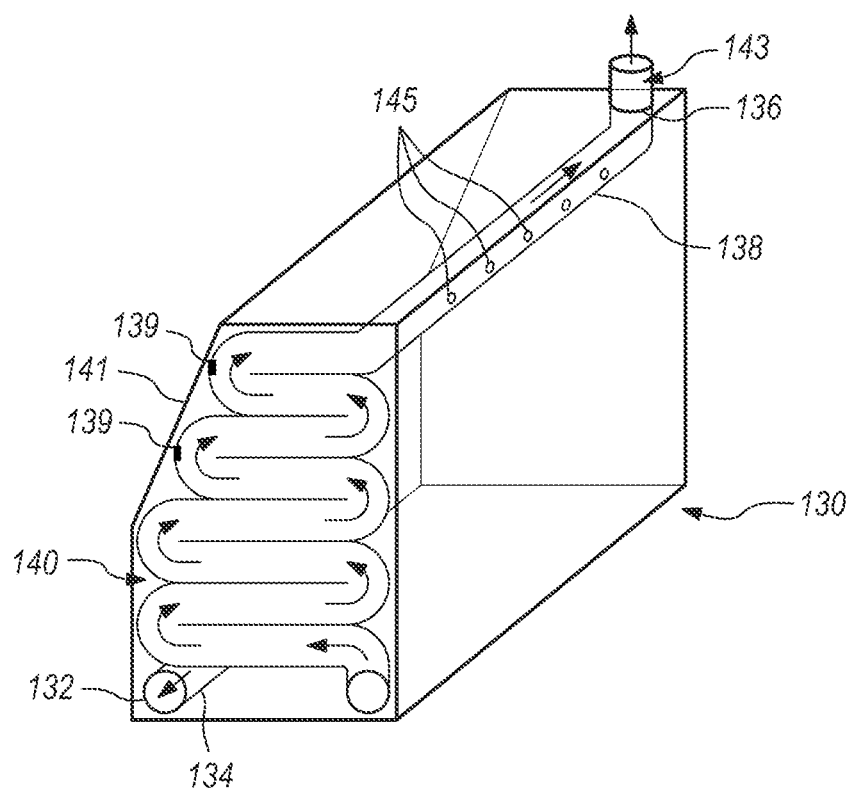
FIG. 5 is an isometric view of a an air processing unit (APU) in accordance with certain embodiments.

With reference to FIG. 5, in certain embodiments, system 100 includes air processing units APU 130R and APU 130L (collectively 130) through which air is circulated, for example for sterilization using ultraviolet light, and/or for heating or cooling as detailed below. Although two APUs 130 are described, fewer (or more) APUs are also possible in the system 100. APUs 130 include an air inlet 132 in communication with an inlet pipe 134 (e.g. 3-inch pipe) at one end, and an air outlet 136 in communication with an outlet pipe 138 at another end. Air is provided to the APUs at the air inlet 132 from the lower main ducts 122 (FIGS. 1 and 3). The pipes 134, 138 extend substantially interiorly of the APU and communicate with a manifold 140 that is configured with suitable baffles and the like to permit the air to be sufficiently exposed to UVC light from one or more UVC bulbs 139 to effectively sterilize it and kill pathogens, such as the Covid-19 virus, during passage of the air through the APU 130. The wavelengths of the light may be specifically selected to target particular pathogens, such as Covid-19, and the number of bulbs and intensity is selected for the required exposure given a particular flow rate of air through the APU. Access to the interior of the APU 130, for example to permit replacement and servicing of UVC bulbs 139, can be facilitated by a providing a removable or openable front or back panels 141. One or more such panels can be transparent to permit viewing for maintenance. Suitable circuit precautions, such as a circuit interrupter (not shown), can also be provided for additional safety.

The pipes 134, 138 in APUs 130 are provided with perforations 145 through which the air passes into or out of the manifold 140, and the perforations can have progressively increasing or decreasing diameters to balance the air pressure so that the air front traversing the manifold 140 is equally distributed and balanced therein. In certain embodiments, one or more fans 143 may be provided proximal the outlet 136, or at other locations, to help draw the air through the APU 130 and facilitate circulation in the system 100.

Figure 6:
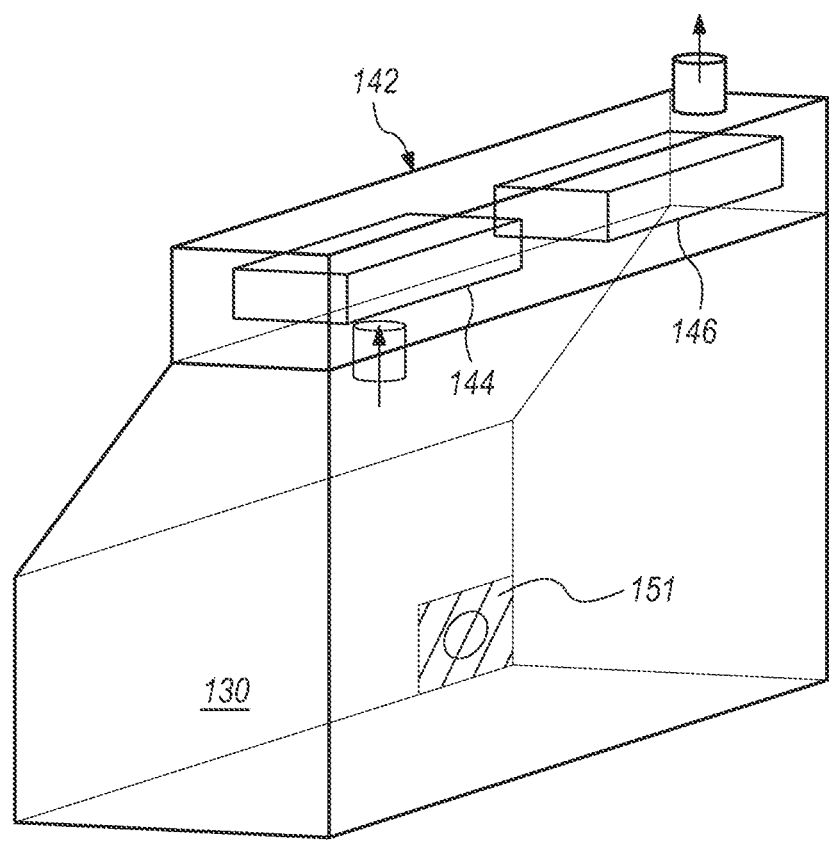
FIG. 6 is an isometric view of an APU equipped with a heat exchange unit in accordance with certain embodiments.

With reference to FIG. 6, in certain embodiments, one or both APUs 130 can each include a heat exchanger module 142, which can house a heater 144 and/or a cooler 146 therein. The heater 144 can operate by way of a heat exchange element (not shown) such as a hot water coil from the bus heater or powered by a standard 12 V DC (direct current) connection. The cooler 146 can also be a DC system and operate by way of an evaporator coil (not shown) coupled to an engine mounted air compressor (not shown). A slide-in air filter bank 151 can be provided in the APU 130 to help remove particulates and clean the circulating air.

Returning to FIG. 1, in certain embodiments, an air door 152 can be provided, in air communication with the system 100, for added security and protection against introduction of pathogens such as Covid-19. The air door 152 operates to further isolate sterilized cabin air from outside air that may be contaminated.

While embodiments and applications have been shown and described, it would be apparent to those skilled in the art having the benefit of this disclosure that many more modifications than mentioned above are possible without departing from the inventive concepts disclosed herein. The invention, therefore, is not to be restricted based on the foregoing description. This disclosure encompasses all changes, substitutions, variations, alterations, and modifications to the example embodiments herein that a person having ordinary skill in the art would comprehend. Similarly, where appropriate, the appended claims encompass all changes, substitutions, variations, alterations, and modifications to the example embodiments herein that a person having ordinary skill in the art would comprehend. Moreover, reference in the appended claims to an apparatus or system or a component of an apparatus or system being adapted to, arranged to, capable of, configured to, enabled to, operable to, or operative to perform a particular function encompasses that apparatus, system, or component, whether or not it or that particular function is activated, turned on, or unlocked, as long as that apparatus, system, or component is so adapted, arranged, capable, configured, enabled, operable, or operative.

What is claimed is:

1. A ventilation system for a vehicle having a cabin for transporting passengers, the ventilation system comprising:
   a segmented plenum disposed above the cabin and comprising a plurality of sub-plenums separated and sealed from one another by partitions;
   a perforated panel attached to the segmented plenum and defining a ceiling of the cabin and having a plurality of perforations for air communication from the segmented plenum to the cabin;
   ductwork comprising:
      one or more upper main ducts extending along a length of the vehicle and in discrete fluid communication with each sub-plenum of the plurality of sub-plenums;
      one or more lower main ducts extending along the length of the vehicle;
      one or more vertical ducts that fluidly connect the one or more upper main ducts to the one or more lower main ducts; and
      one or more seat return ducts that fluidly communicate with the one or more lower main ducts, wherein the upper main ducts, the lower main ducts, the vertical ducts and the seat return ducts communicate with each other to convey air, descending from the segmented plenum through the perforated panel as a high volume, low turbulence blanket of air through the cabin, and back to the segmented plenum;
   an air processing unit (APU) in fluid communication with the ductwork and interposing the one or more upper main ducts and the one or more lower main ducts, the APU being operable to sterilize the air conveyed therein; and
   one or more fans for circulating the air in the ventilation system.

2. The ventilation system of claim 1, wherein the APU includes a heat exchange unit having a heater and/or a cooler.

3. The ventilation system of claim 1, wherein the APU includes one or more UVC bulbs for sterilizing air therein.

4. The ventilation system of claim 1, further comprising an adjustable air balance valve associated with each of the plurality of sub-plenums and controlling airflow thereinto from the one or more upper main ducts.

5. The ventilation system of claim 1, further comprising an air door for isolating the cabin from an exterior of the vehicle.

6. The ventilation system of claim 1, wherein the cabin contains a plurality of passenger seats, each passenger seat having the one or more seat return ducts, comprising a front seat return duct and a back seat return duct that are disposed beneath the seat.

7. The ventilation system of claim 4, wherein the front and back seat return ducts each have an inlet at an aisle end thereof.

8. The ventilation system of claim 6, wherein the front and back seat return ducts each have one or more inlets at intermediate locations along its length and directed at different angles along its perimeter.

9. The ventilation system of claim 8, wherein the one or more inlets at the intermediate locations of a respective seat return duct are directed at different angles along a perimeter of the respective seat return duct.

10. A method for ventilating a cabin of a vehicle comprising:
   drawing in air from the cabin into one or more seat return ducts disposed below one or more seats included within the cabin;
   conveying the air from the one or more seat return ducts to one or more lower main ducts extending along a length of the vehicle;
   receiving the air from the one or more lower main ducts at an air processing unit (APU) and conditioning the air within the APU;
   conveying the air from the APU to one or more upper main ducts extending along the length of the vehicle, the one or more upper main ducts being in fluid communication with a segmented plenum comprising a plurality of sub-plenums separated and sealed from one another by partitions;
   injecting the air separately into each sub-plenum from the one or more upper main ducts;
   balancing air pressure in the plurality of sub-plenums disposed above and separated from the cabin by a perforated panel; and
   ejecting the air from the plurality of sub-plenums through the perforated panel such that a high volume, low turbulence blanket of air descends through the cabin.

11. The method of claim 10, wherein conditioning comprises sterilizing the air with UVC light.

12. The method of claim 10, wherein conditioning comprises performing one or more of circulating, heating, cooling, humidifying, dehumidifying, sterilizing, ionizing, filtering, augmenting or replacing with exterior air.

13. The method of claim 10, wherein drawing in the air from the cabin into the one or more seat return ducts comprises using front and back seat return ducts disposed beneath the one or more seats in the cabin.

14. The method of claim 13, wherein capturing is by way of inlets disposed at aisle ends of the front and back seat return ducts.

15. The method of claim 13, wherein drawing in the air is by way of inlets disposed at intermediate locations along lengths of the front and back seat return ducts and directed at different angles.

16. The method of claim 10, wherein balancing is by way of adjustable air balance valves associated with each sub-plenum and controlling airflow thereinto.

17. A vehicle having a cabin for transporting passengers, the vehicle including:
   a ventilation system comprising:
      a segmented plenum disposed above the cabin and comprising a plurality of sub-plenums separated and sealed from one another by partitions;

a perforated panel attached to the segmented plenum and defining a ceiling of the cabin and having a plurality of perforations for air communication from the segmented plenum to the cabin;

ductwork comprising:
- one or more upper main ducts extending along a length of the vehicle and in discrete fluid communication with each sub-plenum of the plurality of sub-plenums;
- one or more lower main ducts extending along the length of the vehicle;
- one or more vertical ducts that fluidly connect the one or more upper main ducts to the one or more lower main ducts; and
- one or more seat return ducts,
- one or more seat return ducts that fluidly communicate with the one or more lower main ducts, wherein the upper main ducts, the lower main ducts, the vertical ducts and the seat return ducts communicate with each other to convey air, descending from the segmented plenum through the perforated panel as a high volume, low turbulence blanket of air through the cabin, and back to the segmented plenum; and an air processing unit (APU) in fluid communication with the ductwork and interposing the one or more upper main ducts and the one or more lower main ducts, the APU being operable to sterilize the air conveyed therein; and one or more fans for circulating the air in the ventilation system and through the ductwork.

18. The vehicle of claim 17, wherein the APU includes a heat exchange unit having a heater and/or a cooler.

19. The vehicle of claim 17, wherein the APU includes one or more UVC bulbs for sterilizing air therein.

20. The vehicle of claim 17, wherein the cabin contains a plurality of passenger seats, each passenger seat having a front seat return duct and a back seat return duct that are disposed beneath the seat, each seat return duct having an inlet at an aisle end thereof and one or more inlets at intermediate locations along its length and directed at different angles along its perimeter.

21. The vehicle of claim 17, wherein the ventilation system further includes an adjustable air balance valve associated with each sub-plenum and controlling airflow thereinto from an upper main duct.

22. The vehicle of claim 17, further comprising an air door for isolating the cabin from an exterior of the vehicle.

* * * * *